United States Patent [19]

Fine

[11] Patent Number: 4,667,685
[45] Date of Patent: May 26, 1987

[54] GONIOMETRIC FEEDBACK DEVICE AND METHOD FOR MONITORING ANGLES OF BODY JOINTS

[76] Inventor: Edward J. Fine, 183-5 Palmdale St., Williamsville, N.Y. 14221

[21] Appl. No.: 778,807

[22] Filed: Sep. 23, 1985

[51] Int. Cl.$^4$ .............................................. A61B 5/10
[52] U.S. Cl. .................................... 128/782; 128/905
[58] Field of Search ....................... 128/774, 782, 905; 33/511–512; 340/573

[56] References Cited

U.S. PATENT DOCUMENTS

| | | | |
|---|---|---|---|
| 4,110,918 | 9/1978 | James et al. | 128/905 X |
| 4,122,840 | 10/1978 | Tsuchiya et al. | 128/905 X |
| 4,436,099 | 3/1984 | Raftopoulos | 128/782 |
| 4,483,342 | 11/1984 | Pfeifer | 128/653 |
| 4,493,328 | 1/1985 | Saito | 128/905 X |
| 4,549,555 | 10/1985 | Fraser et al. | 128/782 |
| 4,557,275 | 12/1985 | Dempsey | 128/782 |
| 4,571,834 | 2/1986 | Fraser et al. | 128/782 X |

FOREIGN PATENT DOCUMENTS

| | | | |
|---|---|---|---|
| 83/02052 | 6/1983 | PCT Int'l Appl. | 128/781 |
| 0719635 | 3/1980 | U.S.S.R. | 128/782 |
| 0997674 | 2/1983 | U.S.S.R. | 128/782 |
| 1053819 | 11/1983 | U.S.S.R. | 128/782 |

OTHER PUBLICATIONS

Chao et al.; "Electrogoniometer for the Measurement of Human Elbow Joint Rotation"; *J. of Biomech. Eng.*, vol. 102; 11—1980, pp. 301-310.

Townsend et al.; "Total Motion Knee Goniometry"; *J. Biomechanics*, vol. 10, No. 3, 1977, pp. 183-193.

Gransberg et al.; "Computer Programmed System for the Analysis of Active and Passive Isokinetic Movements"; IEEE 1980 Frontiers of Engr. in Health Care; 9—1980, pp. 292-295.

Thomas et al.; "An Electrogoniometer for the Finger"; *Amer. J. of Med. Electronics;* 4—6/1964, pp. 96-100.

*Primary Examiner*—Kyle L. Howell
*Assistant Examiner*—Angela D. Sykes
*Attorney, Agent, or Firm*—Christel, Bean & Linihan

[57] ABSTRACT

A goniometric feedback device and an associated method for monitoring the relative angular position of two human body portions hinged at a common joint utilize a brace mechanism, transducer circuits, an array of selection light-emitting diodes (LEDs), an array of movement response LEDs, indicia associating with each LED array with a series of angular values, preselection circuits and sensing circuits. The brace mechanism includes two brace sections securable to the two body portions, and the transducer circuits provide an output electrical signal which varies in strength in response to a change in the relative angular position between the two brace sections so that the output signal strength corresponds to the relative angular position between the two brace sections. The preselection circuits permit one LED in the array of selection LEDs to be activated to indicate to a user a target angular displacement which the user subsequently attempts to achieve by moving the two body portions, and hence the two brace sections, relative to one another. The sensing circuits sense the strength of the output signal and activate an LED in the array of movement response LEDs which corresponds to the relative angular position of the two brace sections for providing information to the user of progress toward achieving target angular displacement. Additional circuits in the device provide READY and GO signals to the user, provide the user with an audible signal when the angular displacement of the body portions exceeds the target angular displacement by a predetermined angular displacement, and permit the device to be connected to a recording instrument for recording a plot of relative angular position of the two body portions with respect to time.

31 Claims, 7 Drawing Figures

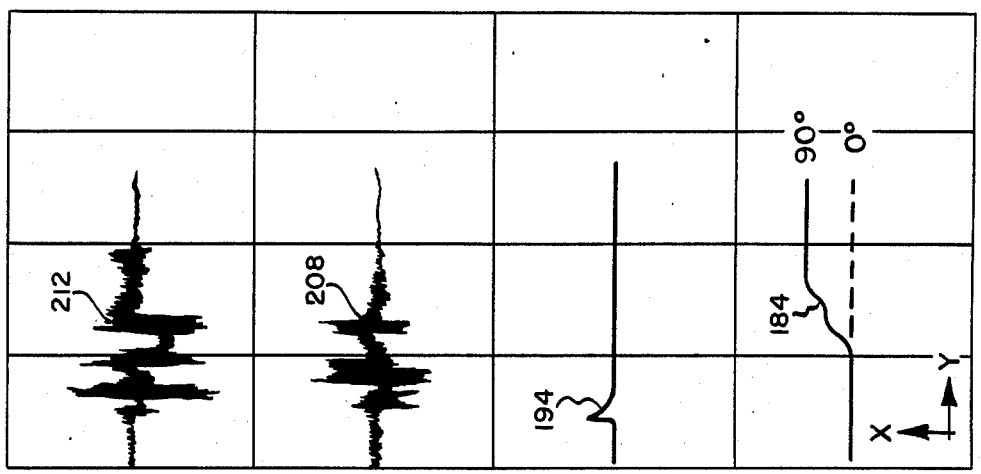
Fig. 7. BALLISTIC MOVEMENTS OF PATIENT WITH PARKINSON'S DISEASE
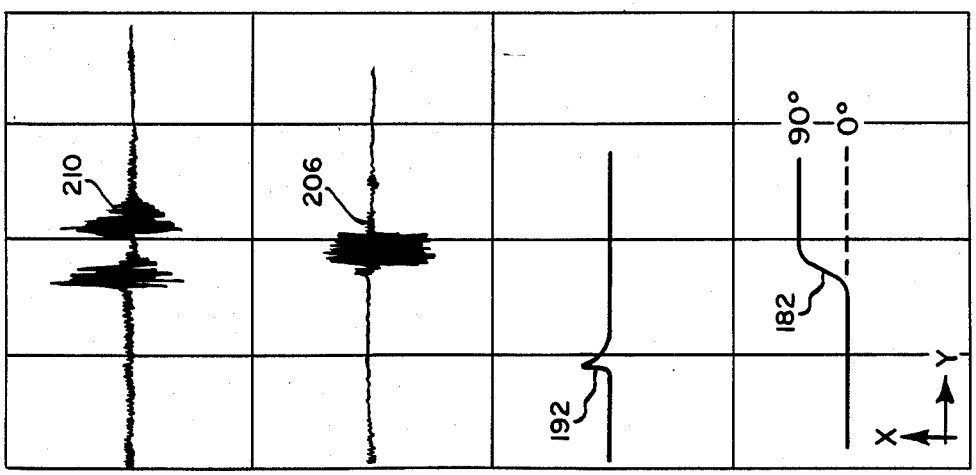
Fig. 6. NORMAL BALLISTIC MOVEMENT 0–90°

GONIOMETRIC FEEDBACK DEVICE AND METHOD FOR MONITORING ANGLES OF BODY JOINTS

BACKGROUND OF THE INVENTION

This invention relates generally to anatomical goniometry and, more particularly, is concerned with a device and method for monitoring the relative angular position of two human body portions hinged at a common joint.

There exists apparatus for an providing an output electrical signal representative of the relative angular position between two human body portions hinged at a common joint. Such apparatus commonly includes two hinged brace members which are each securable to a corresponding one of the two body portions and associated circuitry providing an electrical signal representative of the relative angular position between the two brace members. One such apparatus, shown and described in U.S. Pat. No. 4,436,099, utilizes the provided electrical signal for displaying the relative position between the two brace members in terms of angular degrees. Another such apparatus, described and shown in U.S. Pat. No. 3,020,639, utilizes the provided electrical signal for providing a visual record of the relative motion between the two body portions with respect to time.

It is an object of the present invention to provide a new and improved device and method for monitoring the relative angular position between two body portions hinged at a common joint.

Another object of the present invention is to provide such a device enabling a user to monitor progress while voluntarily moving two hinged body portions relative to one another toward a preselected target angle.

Still another object of the present invention is to provide such a device which can be interfaced with any of several instruments, such an oscilloscope, strip recorder or computer for analysis of the relative movements between the two body portions.

Yet still another object of the present invention is to provide such a device for use with recording instruments and an associated method for accurately recording a plot of the relative angular position between the two body portions with respect to time.

A further object of the present invention is to provide such a device and associated method facilitating analysis of relative angular displacement between two body portions and electromyographic activity of agonist and antagonist muscles of the body portions.

SUMMARY OF THE INVENTION

This invention resides in a device and method for monitoring the relative angular position of two human body portions hinged at a common joint.

The device of the invention includes a brace mechanism including two brace sections hingedly connected for movement relative to one another. The brace sections are securable to two body portions hinged at a common joint so that pivotal movement of the body portions relative to one another moves the two brace sections relative to one another. The device further includes transducer means associated with the brace mechanism for providing an output electrical signal and varying a characteristic of the output signal in response to a change in the relative angular position between the two brace sections so that the output signal characteristic corresponds to the relative angular position between the two body sections. An array of selection indicator elements and an array of movement response indicator elements are also included in the device, and indicia means are associated with each element array so that each indicator element is designated by one of a series of angular values through which the two body portions can be pivotally moved relative to one another.

In order to monitor the relative angular position of two hinged body portions with the device of this invention, the transducer means are placed in operative association with the two body portions so that the characteristics of the output signal varies in response to a change in the relative angular position between the two body portions. One element in the array of selection indicator elements is then activated to indicate to a user a target angular displacement which the user subsequently attempts to achieve by moving the two body portions relative to one another. The output signal of the transducer means is applied to the array of movement response indicator elements in a manner energizing an element in the movement response array corresponding to the characteristic of the output signal for providing information to the user of progress toward achieving the target angular displacement.

BRIEF DESCRIPTION OF THE DRAWINGS

FIG. 6 is a plot of normal EMG activity as two body portions are moved relative to one another.

FIG. 7 is a plot of abnormal EMG activity as two body portions are moved relative to one another.

DETAILED DESCRIPTION OF ILLUSTRATIVE EMBODIMENTS

Figure 1:
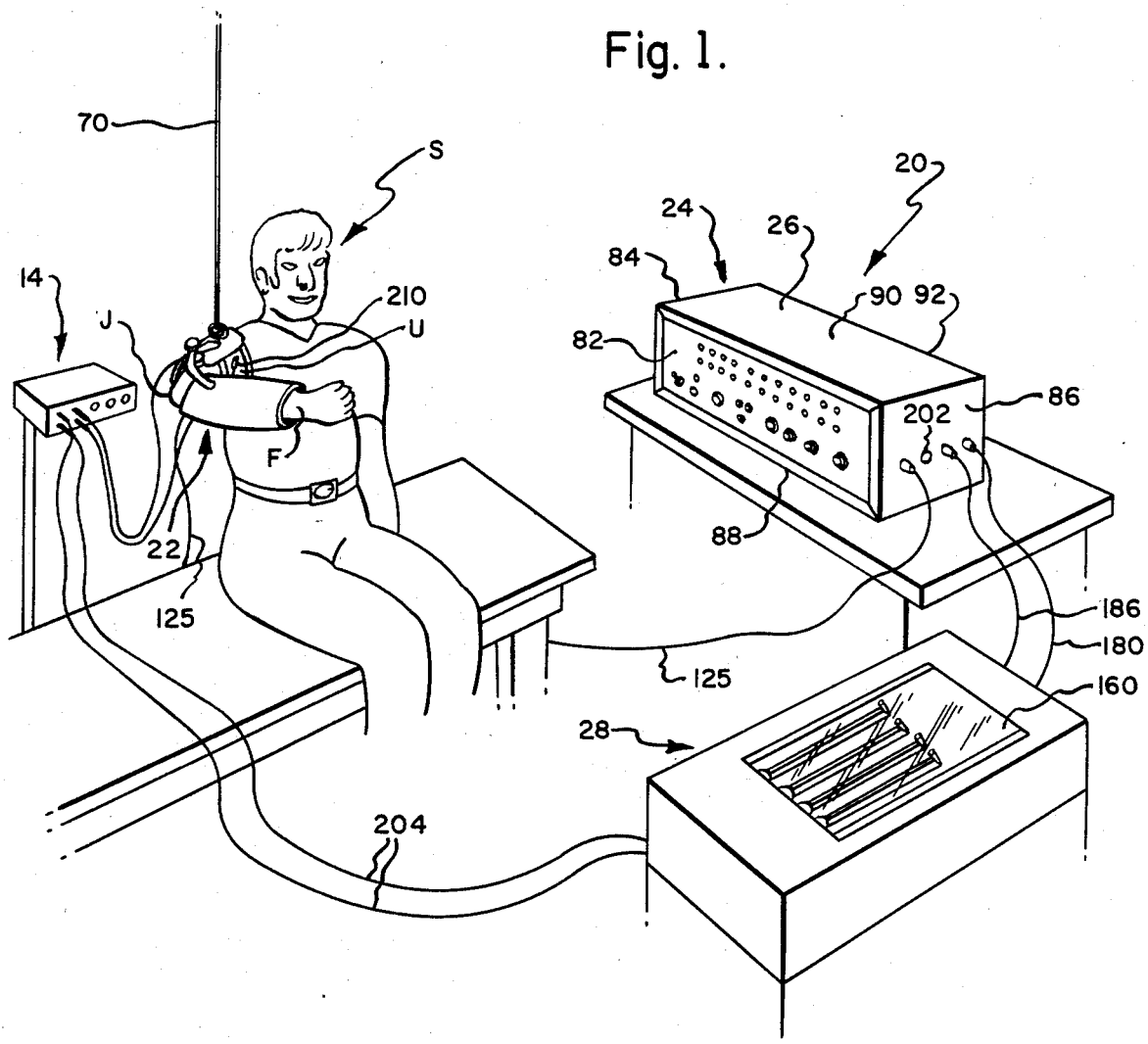
FIG. 1 is a perspective view of an embodiment of the device of this invention shown utilized with a recording instrument.

Turning now to the drawings in greater detail and considering first FIG. 1, there is shown an apparatus, generally indicated 20, in accordance with the present invention and being utilized in a laboratory setting for monitoring the relative movements of two body portions, or arm U and forearm F, of a subject S, which body portions are hingedly connected to one another at a common joint J. In addition to the apparatus 20, there is shown a conventional recording instrument 28 and an electromyographic (EMG) signal amplifier 14. As will be described in greater detail hereinafter, appropriate connections are made between the subject S, apparatus 20, recording instrument 28 and amplifier 14 for recording a plot of the relative angular movements between the arm U and forearm F and plots of attendant EMG activity.

The apparatus 20 includes a brace mechanism 22 releasably secured to the arm U and forearm F, circuit means, generally indicated 24, and a control box 26 in which is housed a large portion of the circuit means 24.

As will be explained in greater detail hereinafter, the circuit means 24 includes means by which a target angular displacement is preselected, which target displacement the subject S attempts to achieve by pivotally moving his body portions U and F relative to one another. By observing and listening to the control box 26, the subject S is provided with visual and audible feedback of his progress toward achieving the target angular displacement.

Figure 2:
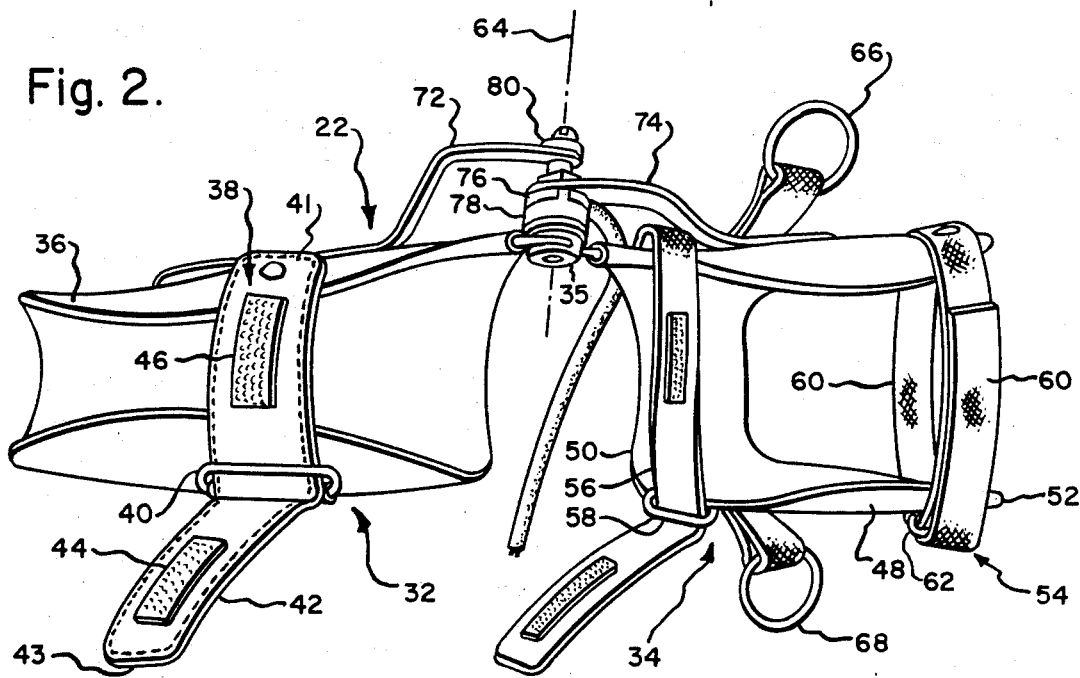
FIG. 2 is a side elevation view of the brace mechanism of the FIG. 1 device.

With reference to FIGS. 1 and 2, the brace mechanism 22 includes two brace sections 32,34 which are hingedly connected by means of a hinge 35. Each brace section 32 or 34 is adapted to be releasably secured to a corresponding one of the arm U and forearm F. More specifically, brace section 32 includes a saddle portion 36 defining an interior surface conforming substantially to the contour of the subject's forearm F and attachment means, generally indicated 38, for releasably securing the saddle portion 36 about the forearm F. The saddle portion 36 is constructed of a malleable plastic material, and the attachment means 38 includes a loop 40 attached to the bottom of the saddle portion 36 and a fabric strap 42 attached at one end 41 to the top of the saddle portion 36. The free end, indicated 43, of the strap 42 is adapted to be inserted through the loop 40 when securing the brace section 32 about the forearm F and to be folded back upon itself to releasably secure the strap 42 through the loop 40. To effect the aforedescribed releasable securement, a hook and loop fastener of the type, for example, manufactured and sold under the tradename Velcro includes a hook strip 44 and a loop strip 46 sewn onto the strap 42. In particular, the hook strip 44 is sewn to one side of the strap 42 adjacent the free end 43, and the loop strip 46 is attached to said one side of the strap 42 adjacent its attached end 41.

It follows from the above that in order to secure the brace section 32 to the forearm F, the forearm F is initially inserted within the saddle portion 36 and the free end 43 of the strap 42 is inserted through the loop 40. The strap free end 43 is then pulled through the loop 40 to bring the top and bottom of the saddle portion 36 firmly against the forearm F. At that point, the hook strip 44 is pressed against the loop strip 46 to secure the relative position of the strap 42 in relationship to the loop 40 to thereby secure the saddle portion about the forearm F.

The brace section 34 includes a saddle portion 48 having two ends 50 and 52 and attachment means, generally indicated 54, for releasably securing the saddle portion 48 about the arm U. The saddle portion 48 is constructed of a malleable plastic material and is formed with a U-shaped cutout, as shown in FIG. 2, so that its inner surface conforms substantially to the contour of the subject's arm U. The attachment means 54 includes one fabric strip 56 and a loop 58 associated with one end 50 of the saddle portion 48 and includes two fabric strips 60,60 and two loops 62 (only one shown) associated with the other end 52 of the saddle portion 48. Each loop 58 or 62 is attached to the bottom of the saddle portion 48, and one end of each strap 56 or 60 is attached to the top of the saddle portion 48. The straps 60,60 drape across opposite sides of the saddle portion 48 as shown, and hook and loop type fastener strips are appropriately sewn to the strap 56,60 in a manner similar to that of strap 42 of brace section 32 for releasably securing the ends 50 and 52 of the saddle portion 48 about the arm U.

In order to secure the brace section 34 to the arm U, the arm is initially inserted within the saddle portion 48 and the strips 56,60 and 60 are inserted through the corresponding loops 58 and 62. The straps 56,60 and 60 are subsequently pulled through the corresponding loops and folded back upon themselves to releasably secure the brace section 34 to the arm U.

With reference still to FIGS. 1 and 2, the hinge 35 of the brace mechanism 22 includes two hinged portions each fixedly secured to the corresponding one of the saddle portions 36 and 48 to permit the brace sections 32 and 34 to pivotally move relative to one another about a pivot axis 64. When the brace sections 32 and 34 are operatively secured about the forearm F and arm U, the pivot axis 64 aligns with a pivotal axis of the elbow joint J so that the forearm F and arm U can pivotally move relative to one another in a manner unhampered by the brace mechanism 22.

The brace mechanism 22 further includes two loops 66 and 68 fixedly attached to the top and bottom, respectively, of the saddle portion 48 of the brace section 34. Each loop 66 or 68 provides means by which the brace mechanism 22, when operatively attached to the subject's forearm F and arm U, can be suspended from a cord 70 (FIG. 1) attached to a ceiling or fixed supporting overhead structure so that the pivot axis 64 of the brace mechanism 22 is oriented substantially vertically. By suspending the brace mechanism 22 and orienting the pivot axis 64 vertically, the brace sections 32 and 34 are permitted to move relative to one another within a horizontal plane and the relative movements between the forearm F and arm U are not significantly effected by gravity. It will be understood that the loop 66 permits the brace mechanism 22 to be suspended as aforesaid when operatively secured to a subject's right arm and forearm, and the loop 68 permits the brace mechanism 22 to be suspended as aforesaid when the brace mechanism 22 is operatively secured to the subject's left arm and forearm.

With reference to FIG. 2, the brace mechanism 22 further includes lever members 72,74 to which is secured a linear potentiometer 76 having a casing 78 and a wiper shaft 80. One end of each lever member 72 or 74 is fixedly attached, as with rivets, to the top of a corresponding one of saddle portions 36 and 48 and its other end is fixed to the potentiometer 76. In particular, the lever member 72 is attached to the wiper shaft 80 for movement therewith, and the lever member 74 is attached to the casing 78 for movement therewith. The casing 78 is suitably connected to the hinge 33 so that the wiper shaft 80 and the casing 78 are pivotally movable relative to one another about the pivot axis 64. Thus, angular displacement of the brace sections 32 and 34 relative to one another pivotally moves the wiper shaft 80 and casing 78 relative to one another through a corresponding amount.

Figure 3:
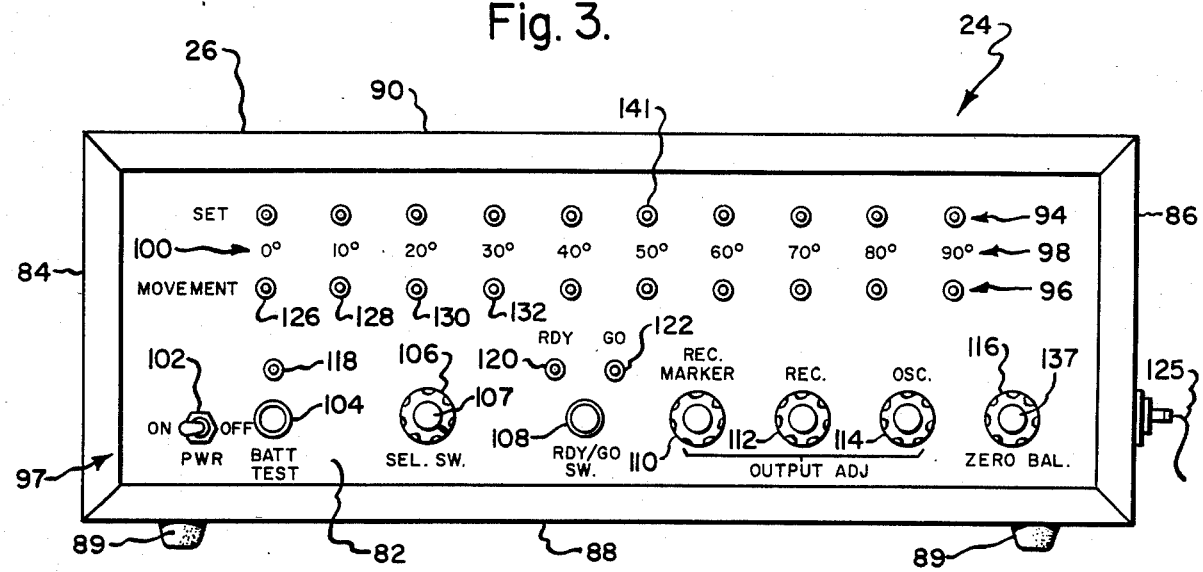
FIG. 3 is a front elevation view of the control box of the FIG. 1 embodiment.

With reference to FIGS. 1 and 3, the control box 26 is in the form of a rectangular box including a front control panel 82, two opposite side panels 84,86, a bottom panel 88, a top panel 90 and a back panel 92. Attached to the bottom panel 88 and protruding downwardly therefrom are elastomeric studs 89,89 which provide suitable feet for the control box 26.

As best shown in FIG. 3, the control panel 82 includes a linear array 94 of selection indicator elements in the form of light emitting diodes (LEDs), a linear array 96 of movement response indicator elements in the form of LEDs, a plurality of switches 97 hereinafter described, and indicia means 98 identifying the arrays 94,96 of LEDs and switches 97. In the apparatus 20, the array 94 includes LEDs which are red in color and the array 96 includes LEDs which are green in color. Each array 94 or 96 of LEDs has two opposite ends and is positioned adjacent or beside the other array 96 or 94 of LEDs so that each light in one array 94 or 96 is associated with a corresponding LED in the other array 96 or 94.

Indicia means 98 includes the word SET to identify the array 94 of selection LEDs and the word MOVEMENT to identify the array 96 of response LEDs, and further includes a row or series 100 of angular values associated with the arrays 94,96 of LEDs. The series 100 includes ten angular values ranging from zero to ninety degrees wherein each value is a multiple of ten degrees. Each value in the series 100 suitably associates or designates one LED in one array 94 or 96 and its corresponding LED in the other array 96 or 94 with one angular value, and as shown in FIG. 3, the values of the series 100 are arranged in sequential order from one end of each array 94 or 96 to the other end. Furthermore, the angular values of the series 100 are within a range of angular values through which the brace sections 32 and 34 can be moved relative to one another and through which the arm U and forearm F can be moved relative to one another.

The plurality of switches 97 mounted in the control panel 82 includes an on/off switch 102, a battery test switch 104, a selection switch 106, a ready/go switch 108, output adjustment switches 110,112, 114 and a zero balance switch 116. The selection switch 106 includes a rotatable knob 107 and is a nine-positional switch so that the knob 107 is adapted to be releasably held in any of nine rotational positions. A green LED 118 is positioned above and associated with the battery test switch 104 and a yellow READY LED 120 and a green GO LED 122 are positioned adjacent and associated with the ready/go switch 108.

Figure 4:
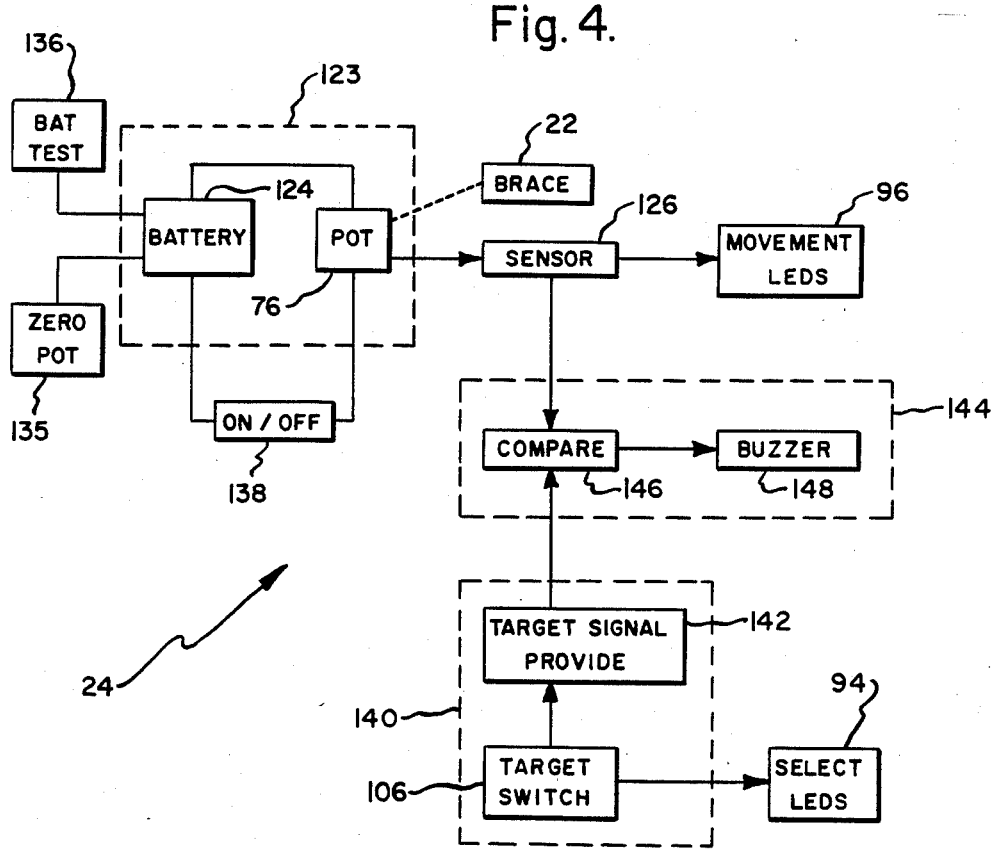
FIG. 4 is a view showing in block diagram form the control circuit for the feedback operation of the FIG. 1 device.

With reference to FIG. 4, and in accordance with the apparatus of this invention, the circuit means 24 includes transducer means 123 including a battery 124 for providing an output electrical signal and the potentiometer 76, previously introduced for varying the strength of the output signal in response to a change in the relative angular position between the brace sections 32,34 so that the output signal strength corresponds to the relative angular position between the two brace sections 32,34. The battery is mounted in the control box 26 (FIG. 1) and is appropriately wired to the potentiometer 76 by means of a cable 125 so that pivotal movement of the potentiometer wiper shaft 80 (FIG. 2) and casing 78 relative to one another varies the strength of the electrical signal provided by the battery. Thus, pivotal movement of the subject's forearm F and arm U relative to one another so that the wiper shaft 80 and casing 78 move relative to one another correspondingly adjusts the strength of the output electrical flow signal. Therefore, the strength of the output electrical signal corresponds to the relative angular position between the forearm F and arm U.

The circuit means 24 further includes sensing means 126 appropriately connected to the transducer means 123 and array 96 of movement LEDs for the sensing strength of the output electrical signal and activating one LED in the movement array 96 of LEDs corresponding to the relative angular position between the two braces 32 and 34. The sensing means 126 includes means for providing a generated signal corresponding to the strength of the output signal for a reason hereinafter set forth.

With reference again to FIG. 3 and as mentioned above, the array 94 of movement LEDs is designated with a series 100 of angular values ranging from zero to ninety degrees. Each value in the series 100 designates an LED in the movement array 96 with an angle of displacement of the forearm F as measured from a position at which the forearm F is extended. Thus, when the forearm F is moved from an extended position through thirty degrees of displacement, the LED indicated 132 in the movement array 96 is activated.

The sensing means 126 further includes means for activating all of the LEDs in the movement array 96 designated to be less than or equal to the angle of displacement of the forearm F. Thus, as the forearm F is moved from an extended condition to a flexed condition through, for example, thirty degrees of displacement, the LEDs indicated 126, 128, 130 and 132 designated 0, 10, 20 and 30 degrees, respectively, are sequentially energized and stay energized until the angle of displacement of the forearm F falls below the angular value designated by the corresponding LED 132,130 or 128. Thus, the movement array 96 of LEDs are adapted to provide information in the form of visual feedback to the patient P of the angular position of the forearm F in relationship to the arm U at any instant of time.

With reference to FIGS. 3 and 4, the circuit means 24 further includes on/off means 138 for turning the apparatus 20 on and off. The on/off means 138 includes the on/off switch 102 appropriately wired to the battery 124. The circuit means 24 still further includes zeroing means 135 including the switch balance knob 116 having a rotatable knob 137 for zeroing the potentiometer 176. The zeroing means 135 is appropriately connected to the transducer means 123 in a manner well known in the art for adjusting the reference electrical signal when the forearm F and upper arm U is in a predetermined, or initial, position. In the apparatus 20, the potentiometer 76 is zeroed by initially extending the forearm F and rotating the zero balance knob 137 in an appropriate rotational direction to a position at which the LED indicated 126 and designated zero degrees in the movement array 96 of LEDs is either activated and rotation of the knob 116 in one rotational direction shuts the LED 126 off or the LED 126 is off and rotation of the knob 137 in the other rotational direction activates the LED 126.

The circuit means 24 further includes battery test means 136 appropriately connected to the battery 124 permitting the subject S or an operator to periodically check the strength of the battery 124 to determine whether the battery strength is at least as high as a predetermined value. The battery test means 136 includes the battery test switch 104 and the battery test LED 118. The test switch 104 is of a momentary pushbutton type and is appropriately wired to the battery 124 so that when the switch 104 is in its normally extended condition, the battery test LED 118 is off and so that when the switch 104 is depressed and the battery output voltage is at least, for example, sixteen volts, the LED 118 is activated. If the LED 118 fails to light up when the switch 104 is depressed, the battery 124 should be replaced.

With reference still to FIGS. 3 and 4, the circuit means 24 includes preselection means 140 for activating one LED in the selection array 94 of LEDs for indicating to the subject S a target angular displacement which the subject attempts to achieve by pivoting the forearm F and arm U relative to one another. The preselection means 140 includes the selection switch 106 and associated circuitry wired between the switch 106 and the selection array 94 of LEDs so that the rotation of the selection knob 107 to one of the nine switch positions activates a corresponding LED in the array 94. Thus, for example, if it is desired that the subject S pivotally move his forearm F through fifty degrees of angular displacement, the selection knob 107 is appropriately positioned so that the LED indicated 141 is activated.

The preselection means 140 further includes means, indicated 142, in FIG. 4, for providing a target signal corresponding to the target angular displacement value for a reason which will be hereinafter set forth.

Referring again to FIG. 3, it will be understood from the above that the apparatus 20 provides information in the form of visual feedback to the subject S of progress toward achieving a target angular displacement. Once the target angular displacement is selected by activating a desired LED in the selection array 94 and a monitoring operation commences, the LEDs in the movement array 96 are sequentially activated from the left end as shown in FIG. 3 as the forearm F is moved toward the target displacement. As soon as the movement LED corresponding to the activated selection LED is activated, the subject S is informed that the target displacement is obtained. If the forearm F overshoots the target displacement by ten degrees or more, the movement LED designated ten degrees higher than the target displacement is activated and indicates to the subject S that the arm displacement is excessive. Thus, by viewing the array 96 of movement response LEDS, the subject S can monitor progress toward achieving the target angular displacement indicated by the selection array 94 of LEDS.

The circuit means 24 further includes means indicated 144 in FIG. 4, for audibly indicating to the subject S that the displacement between the forearm F and the arm U has exceeded the target angular displacement by a predetermined amount. In the apparatus 20, the audible signal generating means 144 includes circuits 146 for receiving and comparing the generated signal from the sensing means 126 and the target signal provided by the target signal-providing means 142 and further includes a buzzer 148. If, by comparing the generated and target signals, the circuits 146 determine that the target displacement has been exceeded by five degrees, the circuits 146 activate the buzzer 148. Thus, the audible signal generating means 144 provides the subject S with information in the form of an audible signal that the actual displacement between the forearm F and upper arm U has been exceeded by five degrees.

Figure 5:
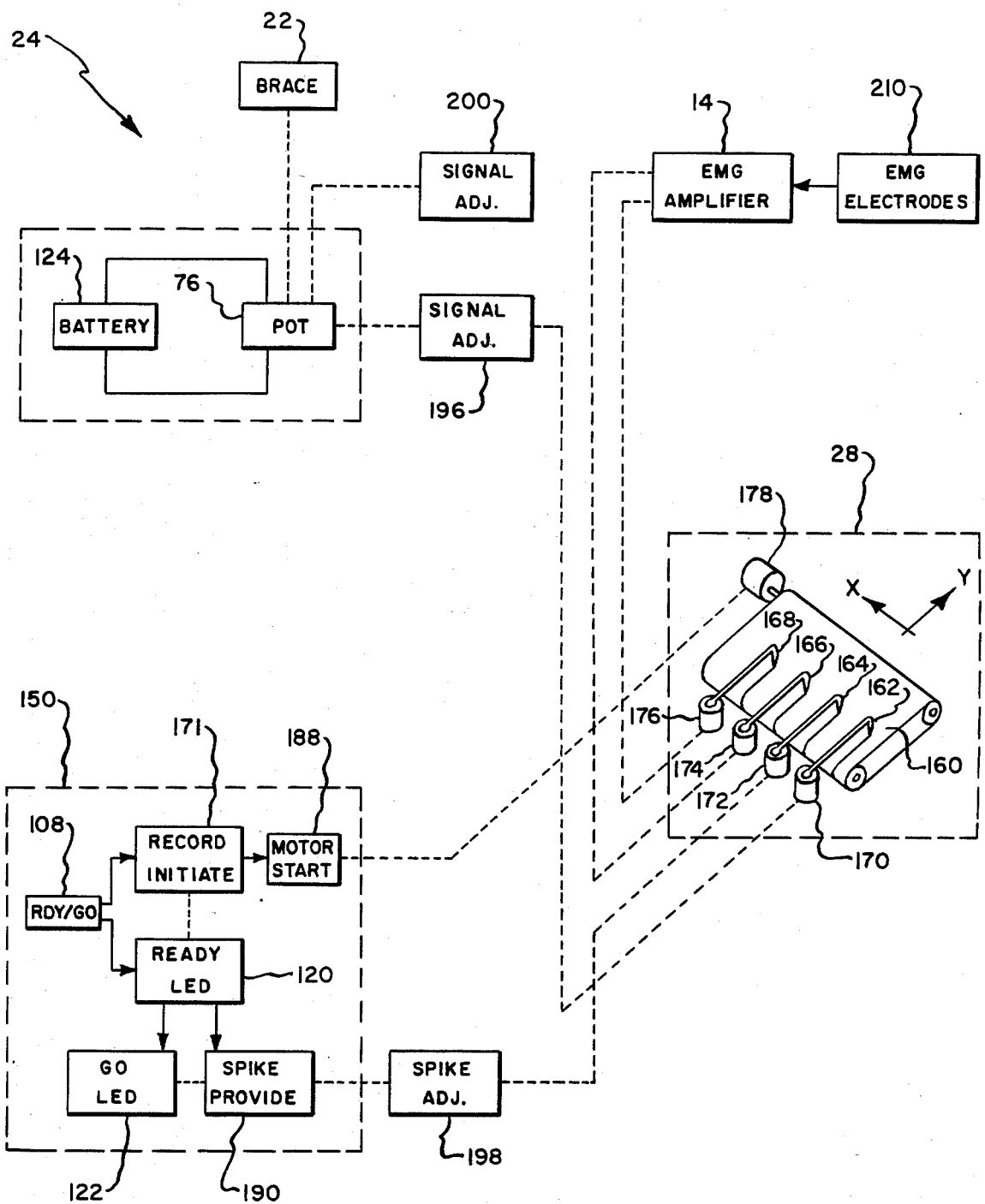
FIG. 5 is a view showing in block diagram form the control circuit for a monitoring operation with the FIG. 1 device and recording instrument.

With reference to FIG. 5, the circuit means 28 further includes READY/GO means 150 for providing a READY signal to the subject S and for providing a GO signal to the subject S following a predetermined lapse of time after the occurrence of the READY signal for indicating to the subject S to begin pivotally moving the arm U and forearm F relative to one another. The READY/GO means 150 include the ready/go switch 108 (FIG. 3) of a push button type, the READY LED 120, the GO LED 122, and appropriate circuitry connected between the switch 108 and LEDS 120 and 122 so that when the switch 108 is depressed, the READY LED 120 is activated and the GO LED 122 is activated about three seconds after the READY LED 120 is activated. Thus, the READY/GO means 150 provides the subject S with a visual READY indication to be prepared to pivotally move the forearm F and a subsequent visual GO indication to the user to begin moving the forearm F.

The READY/GO means 150 includes means enabling the apparatus 20 to be utilized with a secondary monitoring apparatus such as the conventional strip recorder 28 of FIG. 1 for recording an accurate and permanent plot of the relative angular positions of the forearm F and arm U with respect to time. With reference to FIGS. 1 and 5, the strip recorder 28 includes a sheet of recorder material 160 having a portion supported in a spread condition in X and Y coordinate directions for marking thereon and marking means in the form of four recorder markers 162, 164, 166, 168 engaging the sheet 160 and supported for movement relative to and across the sheet 160 in the X-coordinate direction. The recorder 28 further includes first, second, third, and fourth means 170, 172, 174, 176, respectively, for moving the markers 162, 164, 166, 168, respectively, relative to the sheet 160 in the X-coordinate direction in response to input signals hereinafter described. The recorder 28 further includes another means 178 for moving the sheet 160 relative to the marking means in the Y-coordinate direction at a constant translational speed. The another means 178 for moving is provided by a servomotor and is adapted to obtain the constant translational speed between the sheet 160 and marking means moments after start-up.

The first means 170 for moving is appropriately connected to the transducer means 123 by means of the cable 180 conducting the signal output the transducer means 123 and moving the marker 162 relative to the sheet 160 of recorder material in the X-coordinate direction in response to the sensed signal. Thus, the movement of the marker 162 in the X-coordinate direction as the sheet 160 moves at constant translational speed relative to the marker 162 records a plot of the relative angular position of the forearm F and arm U with respect to time. There are shown in FIGS. 6 and 7 illustrative plots 182,184 of relative angular position between forearms and arms as the forearms are moved through ninety degrees of displacement.

The READY/GO means 150 is connected to the recorder 28 by means of a cable 186 (FIG. 1) and includes means 171 for activating the recorder 28 and means 188 for energizing the moving means 178 the instant the READY LED 120 is activated so that the sheet 160 is moved relative to the marking means in the Y-coordinate direction. The READY/GO means 150 further includes circuit means 190 appropriately wired to the READY/GO switch 108 for sending a flow signal spike to the second moving means 172 the instant the GO signal is provided. The circuit means 190 is connected to the second moving means 172 by means of the cable 186, and includes a capacitor (not shown) for providing the flow signal spike upon discharge. The second moving means 172 abruptly moves the marker 164 in response to the flow signal spike relative to the sheet 160 in the X-coordinate direction to mark the instant that the GO signal is provided. Typically and illustrated by plot 192 of FIG. 6 and 194 of FIG. 7, the flow signal spike provided by the capacitor provides a sharply rising, gradually falling movement of the marker 164.

With a record of the instant at which the GO signal occurs, factors such as the response time of the subject can be analyzed. Furthermore, inasmuch as the moving means 178 requires a moment after start-up to move the sheet 160 and marking means relative to one another in the Y-coordinate direction at constant translational speed, the READY/GO means 150 permit the constant translational speed to be obtained prior to the occurrence of the GO signal. The subsequent plot of the relative angular position of the arm and forearm relative to one another with respect to time is thus very accurate.

With reference to FIGS. 3 and 5, the circuit means 24 further includes means 196 for controlling the length of movement or excursion of the marker 162 on the sheet 160 of recording material in the X-coordinate direction. Such marker control means 196 includes the adjustment switch 112 and means, including a potentiometer, appropriately connected to the switch 112 for varying a characteristic, such as strength of the electrical output signal of the transducer means 123 as the switch 112 is adjusted. The displacement marker control means 196 thus permits the output signal to be controlled to accommodate the capacity of the recorder 28 to receive the output signal or to adjust the excursion length of the marker 162 in accordance with desired boundaries on the sheet 160 of recorder material.

The circuit means 24 further includes means 198 for controlling the strength of the spike signal emitted by the spike signal providing means 190. Such spike signal controlling means 198 includes the adjustment switch 110 and means including a potentiometer, appropriately connected to the switch 110 for varying the strength of the spike signal as the switch 110 is adjusted. The spike signal controlling means 198 thus allows the amplitude of the spike signal to control the excursion of the marker 164 in accordance with desired bounds on the sheet 160 of recorded material.

The circuit means 24 still further includes means 200 connected between the transducer means 123 and the terminal indicated 202 in FIG. 1 for adjusting the strength of the electrical output signal provided by the transducer means 123 and routed to the terminal 202. Such adjustment means 200 include the adjustment switch 114 and means, including a potentiometer, for adjusting the strength of the output signal as the switch 114 is adjusted. The adjustment means 200 permit the apparatus 20 to be interfaced through the terminal 202 with another instrument such as a computer or oscilloscope, and by adjusting the switch 114, the output signal strength can be adjusted to accommodate the signal-receiving capacity of the interfaced instrument.

In order to utilize the apparatus 20 record a plot of the relative angular displacement between the forearm F and arm U with respect to time and with reference to FIGS. 1 and 3-7, the brace mechanism 22 is appropriately connected to the forearm F and arm U of the subject and the circuit means 24 are connected to the recorder 28 as aforesaid. One LED in the selection array 94 of LEDs is then activated by the selection switch 106 to provide a target angular displacement to the subject S. The READY/GO switch 108 is then depressed to activate the READY LED 120 to thereby signal READY to the user and to energize the moving means 178 to begin moving the marker means relative to the sheet 160 in the Y-coordinate direction. The GO LED 122 is subsequently energized and a flow signal spike is sent to the moving means 172 to record a plot similar to plots 192 and 194 of FIGS. 6 and 7 respectively. In response to the energized GO LED 122, the subject S moves the forearm F and arm U to the target angular displacement while the first moving means 170, in response to the strength of the output signal of the transducer means 24, records a plot similar to plots 182 and 184 of FIGS. 6 and 7, respectively, of the relative angular position between the forearm F and arm U with respect to time. While the subject attempts to obtain the target angular displacement, the array 96 of movement response LEDs and the audible signal generating means 144 provide information to the subject S of his progress.

It has been found that the apparatus 20 and recorder 28 are particularly well-suited for obtaining plots of angular movement of the forearm F and arm U while obtaining plots of attendant electromyographic (EMG) signals. To obtain such plots and with reference to FIGS. 1 and 5, the apparatus 20 is appropriately connected between the subject S and the recorder 28 in the manner aforedescribed. Electromyographic electrodes 210 are then connected at one end in a manner well known in the art to the subject's triceps and biceps of the arm U. The other ends of the EMG electrodes are routed through the amplifier 14 to the recorder 28 by means of the wires 204,204. The amplifier 14 is so connected to the recorder 28 that EMG signals sensed by the subject's triceps are sensed by the third moving means 174 and the EMG signals sensed by the subjects biceps are sensed by the fourth moving means 176. Thus, the markers 166 and 168 move relative to the sheet 160 in the X-coordinate direction in response to the signals sensed by the triceps and biceps, respectively.

With reference to FIGS. 6 and 7, there are shown illustrative plots 206,208 of the EMG signals received by the triceps and illustrative plots 210,212 of EMG signals received by the biceps as a function of time and as a function of angular displacement of the forearm F. Such plots facilitate analysis of the movements and attendant EMG activity of a subject.

It will be understood that numerous modifications and substitutions can be made to the aforedescribed embodiments without departing from the spirit of the invention. For example, although the indicator elements of the apparatus 20 have been shown and described in the form of LEDs, it will be understood that arrays of selection and movement response indicators can be in the form of liquid crystal displays. Furthermore, although the circuitry in the read/go means 150 has been described as delaying the GO signal for about three seconds following the occurrence of the READY signal, such circuitry may be constructed to provide a random delay or fixed delay other than three seconds. Accordingly, the aforedescribed embodiments are intended for purposes of illustration and not limitation.

I claim:

1. A goniometric feedback device for monitoring the relative angular position of two human body portions hinged at a common joint, said device comprising:

a brace mechanism including two sections hingedly connected for movement relative to one another, said brace sections being securable to two body portions hined at a common joint so that pivotal movement of the body portions relative to one another moves said two brace sections relative to one another;

transducer means associated with said brace mechanism for providing an output electrical signal and varying a characteristic of said output signal in response to a change in the relative angular position between said two brace sections so that said output signal characterstic corresponds to the relative angular position between said two brace sections;

an array of selection indicator elements;

an array of movement response elements arranged in a side-by-side relationship with the array of selection indicator elements, each of said arrays each of said arrays of elements being arranged in a row having two opposite ends so as to provide two rows of elements arranged in a side-by-side relationship wherein each element in one row corresponds to an adjacent element in the other row;

indicia means including indicia for associating each of said indicator element arrays with a series of angular values so that each indicator element of said element arrays is designated by one of a series of angular values, said series of angular values being within a range of angular displacement values within which the two body portions can be pivotally moved relative to one another and the angular values associated with each element array being arranged in sequential order from one end of each array to the other end of each array;

preselection means associated with said array of selection indicator elements for activating one element in said array of selection indicator elements which indicate to a user a target displacement which the user subsequently attempts to achieve by moving said two brace sections relative to one another, said preselection means including switch means for enabling a user to preselect said target angular displacement;

means associated with the transducer means and said array of movement indicator elements for sensing the characteristic of said output signal and activating an element in said array of movement response indicator elements corresponding to the relative angular position of said two brace sections so that by viewing the relationship between the activated elements in said two arrays of elements, the user is informed of progress toward achieving the preselected target angular displacement.

2. A device as defined in claim 1 wherein said sections of said brace mechanism are hingedly connected for movement relative to one another about a pivot axis and are adapted to be suspended from a fixed supporting structure so that said pivot axis of said brace sections is oriented generally vertically and the relative movement between said brace sections is generally confined to a horizontal plane to eliminate effects of gravity upon movement of said two brace sections relative to one another.

3. A device as defined in claim 1 further including a battery operatively connected to said transducer means.

4. A device as defined in claim 3 further comprising means for testing the voltage of said battery.

5. A device as defined in claim 1 wherein said transducer means includes a linear potentiometer.

6. A device as defined in claim 5 further comprising means for zeroing the potentiometer.

7. A device as defined in claim 1 wherein the indicia designating one element in an element array with one angular value designates one element in the other element array with said one angular value so that each element in one element array corresponds to an adjacent element in the other element array.

8. A device as defined in claim 1 wherein said elements in said selection indicator array include lights for visually indicating to a user the target angular displacement.

9. A device as defined in claim 1 wherein said elements in said movement response indicator array include lights for visually indicating to a user the progress toward achieving the target angular displacement.

10. A device as defined in claim 1 wherein said series of angular values includes angular values provided in equal increments.

11. A device as defined in claim 1 wherein said switch means includes a switch for manually preselecting said target angular displacement.

12. A device as defined in claim 1 further comprising:
first circuit means associated with said preselection means and said transducer means for detecting any overshoot exceeding the target displacement of said two brace sections and for generating an audible signal to the user when the detected overshoot exceeds the target angular displacement by a predetermined amount.

13. A device as defined in claim 12 wherein said preselection means includes means for generating a target signal characteristic corresponding to the target angular displacement and wherein said first circuit means for detecting any overshoot includes second circuit means for comparing the characteristic of the output signal to the target signal characteristic and for producing an audible signal when the output signal characteristic exceeds the target signal characteristic by a predetermined amount.

14. A device as defined in claim 1 further comprising circuit means connected to said transducer means for varying the voltage of said output signal to permit said device to be interfaced with another monitoring instrument.

15. A device as defined in claim 1 utilized with a recording instrument wherein said recording instrument is responsive to the output signals of the transducer means for recording the relative angular positions between the two body portions with respect to time and said device further comprises:
means for providing a READY signal to the user; and
means for automatically providing a GO signal following a predetermined lapse of time after the occurrence of the READY signal for indicating to the user to begin moving the two body portions relative to one another toward the preselected target angular displacement so that an accurate record of the relative angular positions between the two body portions with respect to time is obtained.

16. A device as defined in claim 15 wherein said means for providing a READY signal includes means for energizing the recording instrument to begin a recordation process the instant the Ready signal is provided.

17. A device as defined in claim 15 wherein said means for providing a GO signal includes means for sending a signal to the recording instrument so that the recording instrument marks the instant with respect to time at which the GO signal is provided.

18. An apparatus for recording a plot of the relative angular movement between two body portions hinged at a common joint with respect to time, said apparatus comprising:
a brace mechanism including two sections hingedly connected together for movement relative to one another, said brace sections being securable to two body portions hinged at a common joint so that pivotal movement of the body portions relative to one another moves said two brace sections relative to one another;

transducer means associated with said brace mechanisms for providing an output electrical signal and varying a characteristic of said output signal in response to a change in the relative angular position between said two brace sections so that the output signal characteristic corresponds to the relative angular position between said two brace sections;

an array of selection indicator elements;

an array of movement response indicator elements arranged in a side-by-side relationship with the array of selection indicator elements, each of said arrays of elements being arranged in a row having two opposite ends so as to provide two rows of elements arranged in a side-by-side relationship wherein each element in one row corresponds to an adjacent element in the other row;

indicia means including indicia for associating each of said indicator element arrays with a series of angular values so that each indicator element of said element arrays is designated by one of a series of angular values, said series of angular values being within a range of angular displacement values within which the two body portions can be pivotally moved relative to one another and the angular values associated with each element array being arranged in sequential order from one end of each array to the other end of each array;

preselection means associated with said array of selection indicator elements for activating one element in said array of selection indicator elements which indicate to a user a target angular displacement which the user subsequently attempts to achieve by moving said two brace sections relative to one another, said preselection means including switch means enabling a user to preselect said target angular displacement;

means associated with the transducer means and said array of movement indicator elements for sensing the characteristic of said output signal and activating an element in said array of movement response indicator elements corresponding to the relative angular position of said two brace sections so that vy viewing the relationship between the activated elements in said two arrays of elements, the user is informed of progress toward achieving the preselected target angular displacement;

a recording instrument connected to said transducer means and including a sheet of recorder material, said recording instrument including means responsive to said output signal of said transducer means for plotting the output signal characteristic with respect to time on said sheet of recorder material; and means for commanding the user to begin pivotally moving the two body portions relative to one another so that a plot of relative angular position between the two body portions with respect to time is accurately obtained on said sheet of recorder material as the user attempts to achieve the preselected target angular displacement.

19. An apparatus as defined in claim 18 wherein said means for commanding includes means for providing a READY signal to the user and means for automatically providing a GO signal following a predetermined lapse of time after the occurence of the READY signal.

20. An apparatus as defined in claim 19 wherein said sheet of recorder material is supported in condition for marking thereon, said means responsive to said output signal includes:
 (a) marking means engaging said sheet and supported for movement relative to and across said sheet in generally one coordinate direction;
 (b) one means for moving said marking means relative to said sheet in said one coordinate direction;
 (c) another means for moving said marking means relative to said sheet in another coordinate direction at constant translational speed, the constant translational speed being obtained from zero moments after start-up of said another means for moving and said means for providing a READY signal includes means for energizing said another means for moving the instant the ready signal is provided to achieve constant translational speed.

21. A device as defined in claim 20 further comprising adjustment means connected between said transducer means and said means responsive to said output signal for controlling a characteristic of said output signal to thereby control the excursion length of said marking means relative to said sheet in said one coordinate direction in response to said output signal.

22. A device as defined in claim 20 further comprising adjustment means connected between said means for providing a GO signal and said means responsive to said output signal for controlling a characteristic of said one signal to thereby control the excursion length of said marking means relative to said sheet in said one coordinate direction in response to said one signal.

23. An apparatus as defined in claim 19 wherein said means for providing a GO signal includes means for sending one signal to the recording instrument so that the recording instrument marks the instant with respect to time at which the GO signal is provided.

24. A method for monitoring the relative angular position of two body portions hinged at a common joint, said method comprising the steps of:
 providing transducer means for generating an output electrical signal having a characteristic which varies in response to a change in the relative angular position between the two body portions so that the output signal characteristic corresponds to the relative angular position between the two body portions; and placing said transducer means in operative association with said two body portions;

providing an array of selection indicator elements and an array of movement response indicator elements wherein said arrays of elements are arranged in two side-by-side rows each having two opposite ends and each element in one row corresponds to an adjacent element in the other row and wherein each indicator element array is associated with a series of angular values so that each indicator element of said element arrays is associated with one of the series of angular values, said series of angular values being within a range of angular displacement values within which the two body portions can be pivotally moved relative to one another;

activating one element in said array of selection indicator elements in response to input provided by a user which indicates to a user a target angular displacement which the user sequentially attempts to achieve by moving the two body portions relative to one another;

applying said output signal of said transducer means to said array of movement response indicator elements in a manner energizing an element in said movement response array corresponding to the characteristic of the output signal so that by viewing the relationship between the activated and energized elements of said two arrays of elements, the user is informed of progress toward achieving the target angular displacement.

25. A method as defined in claim 24 wherein said step of applying is followed by the steps of
detecting any overshoot exceeding the target displacement of said two brace sections; and
providing an audible signal to the user when the detected overshoot exceeds the target angular displacement a predetermined amount.

26. A method as defined in claim 25 wherein said step of activating is followed by a step of providing a target electrical signal corresponding to said target angular displacement and said step of detecting any overshoot includes the steps of comparing the provided output signal to the target signal and producing an overshoot electrical signal when the provided output signal by a predetermined amount exceeds the target signal and said step of generating an audible signal includes a step of receiving the overshoot signal.

27. A method for recording a plot of relative angular displacement between two body portions connected at a common joint with respect to time, said method comprising the steps of:
providing transducer means for generating an output electrical signal having a characteristic which varies in response to a change in the relative angular position between the two body portions so that the output signal characteristic corresponds to the relative angular position between the two body portions;
placing said transducer means in operative association with said two body portions;
providing an array of selection indicator elements and an array of movement response indicator elements wherein said arrays of elements are arranged in two side-by-side rows each having two opposite ends and each element in one row corresponds to an adjacent element in the other row and wherein each indicator element array is associated with a series of angular values so that each indicator element of said element arrays is associated with one of a series of angular values, said series of angular values being within a range of angular values within which the two body portions can be pivotally moved relative to one another;
activating one element in said array of selection elements in response to input provided by a user which indicates to a user a target angular displacement which the user subsequently attempts to achieve by moving the two body portions relative to one another;
applying said output signal of said transducer means to said array of movement response indicator elements in a manner energizing an element in said response indicator elements corresponding to the output signal characteristic so that by viewing the relationship between the activated and energized elements of said two arrays of elements, the user is informed of progress toward achieving the target angular displacement;
providing a recording instrument including means responsive to said output electrical signal for recording a plot of relative angular position between the two body portions with respect to time;
sending said output electrical signal to said recording instrument; and
commanding the user to begin pivotally moving the two body portions relative to one another so that an accurate plot of relative angular position between the two body portions with respect to time is obtained as the user attempts to achieve the preselected target angular displacement.

28. A method as defined in claim 27 wherein said step of commanding is preceded by a step of signalling READY to the user and said commanding step includes the step of automatically signalling GO to the user following a predetermined lapse of time after the occurrence of the READY signal.

29. A method as defined in claim 28 wherein said recording instrument includes a sheet of recorder material supported in a condition for marking thereon, said means responsive to said output electrical signal includes marking means engaging said sheet and supported for movement relative to and across said sheet in generally one coordinate direction, one means for moving said marking means relative to said sheet in said one coordinate direction and another means for moving said marking means relative to said sheet in another coordinate direction at constant translational speed, the constant translational speed being obtained from zero moments after start-up of said another means for moving and said step of signalling GO is preceded by the step of energizing said another means for moving the instant the READY signal is provided to achieve constant translation speed.

30. A method as defined in claim 27 wherein said step of commanding includes a simultaneous step of sending one signal to the recording instrument so that the recording instrument marks the instant with respect to the time at which the command is provided.

31. A method for recording corresponding plots of relative displacement between two body portions connected at a common joint with respect to time and attendant myoelectric signals, said method comprising the steps of:
providing myoelectric measuring apparatus for operatively measuring the myoelectric signals attending the movements the two body portions relative to one another and operatively connecting the measuring apparatus to the two body portions;
providing transducer means for generating an output electrical signal having a characteristic which varies in response to a change in the relative angular position between the two body portions so that the output signal characteristic corresponds to the relative angular position between the two body portions;
placing said transducer means in operative association with said two body portions;
providing an array of selection indicator elements and an array of movement response indicator elements wherein said arrays of elemements are arranged in two side-by-side rows each having two opposite ends and each element in one row corresponds to an adjacent element in the other row and wherein each indicator element is associated with one of a series of angular values, said series of angular values being within a range of angular values within which the two body portions can be pivotally moved relative to one another;

activating one element in said array of selection elements in response to input provided by a user which indicates to user a target angular displacement which the user subsequently attempts to achieves by moving the two body portions relative to one another;

applying said output signal of said transducer means to said array of movement response indicator elements in a manner energizing an element in said response indicator elements corresponding to the output signal characteristic so that by viewing the relationship between the activated and energized element of said two arrays of elements, the user is informed of progress toward achieving the target angular displacement;

providing a recording instrument including means responsive to said output electrical signal and the attendant myoelectric signals for recording a plot of relative angular position between the two body portions with respect to time and for recording a plot of myoelectric signals attending the movement of the body portions;

sending said output electrical signal to said recording instrument and operatively connecting the myoelectric measuring apparatus to the recording instrument; and commanding the user to begin pivotally moving the two body portions relative to one another so that an accurate plot of relative angular position between the two body portions with respect to time and a corresponding plot of attendant myoelectric signals is obtained as the user attempts to achieve the preselected target angular displacement.

* * * * *